(12) United States Patent
Auble

(10) Patent No.: US 9,579,233 B1
(45) Date of Patent: Feb. 28, 2017

(54) THERAPUETIC PURSE

(71) Applicant: Cristy Lee Auble, Flagstaff, AZ (US)

(72) Inventor: Cristy Lee Auble, Flagstaff, AZ (US)

( * ) Notice: Subject to any disclaimer, the term of this patent is extended or adjusted under 35 U.S.C. 154(b) by 744 days.

(21) Appl. No.: 13/928,444

(22) Filed: Jun. 27, 2013

Related U.S. Application Data

(60) Provisional application No. 61/665,670, filed on Jun. 28, 2012.

(51) Int. Cl.
    *A61F 7/10*     (2006.01)
    *A61F 7/02*     (2006.01)
    *A45C 3/06*     (2006.01)
    *F25D 3/08*     (2006.01)

(52) U.S. Cl.
    CPC . *A61F 7/02* (2013.01); *A45C 3/06* (2013.01); *F25D 3/08* (2013.01)

(58) Field of Classification Search
    CPC .................................. F25D 3/08; A45C 11/20
    See application file for complete search history.

(56) References Cited

U.S. PATENT DOCUMENTS

| | | | | |
|---|---|---|---|---|
| 2,289,254 A | * | 7/1942 | Eagles | A45C 11/20 220/592.01 |
| 3,995,621 A | | 12/1976 | Fletcher et al. | |
| 4,637,076 A | | 1/1987 | Tartt | |
| 4,699,144 A | | 10/1987 | Sherwood | |
| 5,111,810 A | * | 5/1992 | Fortney | A61F 7/02 602/2 |
| 5,325,969 A | * | 7/1994 | Gordon | A45C 11/20 206/541 |
| 5,429,593 A | | 7/1995 | Matory | |
| 5,472,279 A | * | 12/1995 | Lin | A45C 11/20 383/110 |
| 5,716,388 A | * | 2/1998 | Petelle | A61F 7/02 126/204 |
| 5,779,657 A | | 7/1998 | Daneshvar | |
| 5,800,245 A | | 9/1998 | Barbe-Vicuna et al. | |
| 5,842,571 A | * | 12/1998 | Rausch | A45C 11/20 206/541 |
| 5,904,230 A | * | 5/1999 | Peterson | A45C 11/20 190/107 |
| RE36,869 E | | 9/2000 | Ewen | |
| 6,296,165 B1 | * | 10/2001 | Mears | A45C 3/00 150/107 |
| 6,390,885 B1 | | 5/2002 | Brooks | |

(Continued)

FOREIGN PATENT DOCUMENTS

GB      2483466 A      3/2012

OTHER PUBLICATIONS

Deon Maas, / Sew 'N Share / American Sewing Guild 2006.

*Primary Examiner* — Kaitlyn Smith
(74) *Attorney, Agent, or Firm* — Invention to Patent Services; Alex Hobson

(57) ABSTRACT

A therapeutic purse configured with a therapeutic device including a cushion, or a thermal pouch is provided. The therapeutic purse is an enclosure having an interior volume and at least one opening to the interior volume and a closure feature. In one embodiment, the interior volume of the purse comprises a therapeutic pocket configured for containing a therapeutic device. In yet another embodiment, the therapeutic purse comprises a hot or cold pouch that may comprise a substance that may be transferred into a conduit coupled to the strap.

17 Claims, 7 Drawing Sheets

(56) References Cited

U.S. PATENT DOCUMENTS

| | | |
|---|---|---|
| 6,477,710 B1 | 11/2002 | Ojoyeyi |
| 6,574,800 B1 | 6/2003 | Leger et al. |
| 6,793,112 B2 | 9/2004 | Ammerman |
| 6,926,184 B2 | 8/2005 | Hancock et al. |
| 7,258,593 B2 | 8/2007 | Mineconzo |
| 7,293,295 B2 | 11/2007 | King |
| 7,396,272 B1 | 7/2008 | Newlen |
| 7,753,759 B2 | 7/2010 | Pintor et al. |
| 7,810,172 B2 | 10/2010 | Williams |
| 7,823,221 B2 | 11/2010 | Green |
| 7,905,763 B1 | 3/2011 | Frank |
| D636,974 S | 5/2011 | Gibson |
| 7,942,856 B2 | 5/2011 | Lentini |
| 7,987,524 B2 | 8/2011 | Bower |
| 2003/0149461 A1* | 8/2003 | Johnson .................... A61F 7/02 607/108 |
| 2004/0074936 A1* | 4/2004 | McDonald ......... B65D 81/3888 224/148.5 |
| 2005/0056048 A1* | 3/2005 | Fuchs .................... A45C 11/20 62/457.7 |
| 2005/0072181 A1* | 4/2005 | Mogil .................... A45C 11/20 62/457.7 |
| 2005/0133399 A1* | 6/2005 | Fidrych ..................... A45F 3/04 206/545 |
| 2005/0183446 A1* | 8/2005 | Fuchs .................... A45C 11/20 62/457.7 |
| 2007/0249264 A1 | 10/2007 | Rhodes |
| 2009/0294237 A1* | 12/2009 | Sisitsky ................. A45C 1/024 190/103 |
| 2010/0071395 A1* | 3/2010 | Ledoux ..................... F25D 3/08 62/259.1 |
| 2010/0236953 A1* | 9/2010 | Myers ................. A45C 7/0095 206/223 |
| 2012/0012627 A1* | 1/2012 | Hess ...................... A45C 11/20 224/576 |
| 2014/0191007 A1* | 7/2014 | Demskey ............... A45C 13/30 224/579 |
| 2015/0136824 A1* | 5/2015 | Demskey ................. A45F 3/14 224/576 |
| 2015/0253056 A1* | 9/2015 | Richardson ............... F25D 3/08 62/457.7 |

* cited by examiner

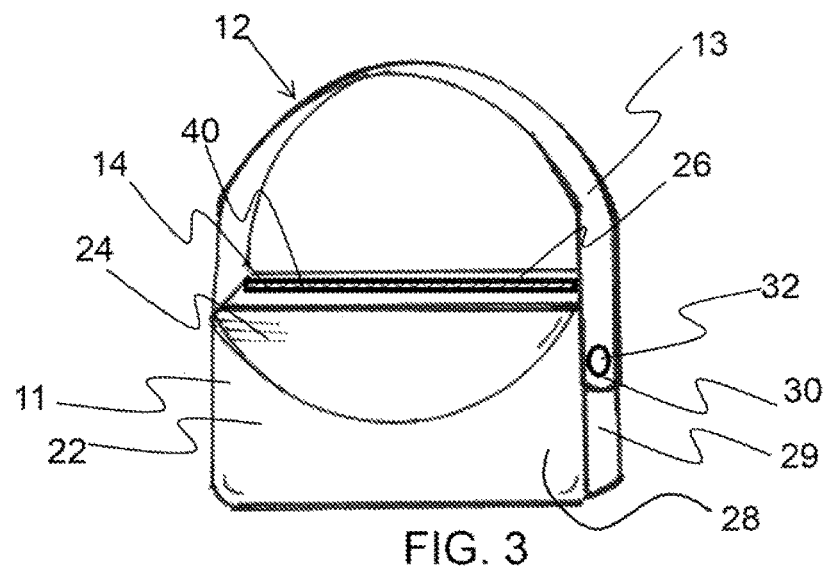
FIG. 3
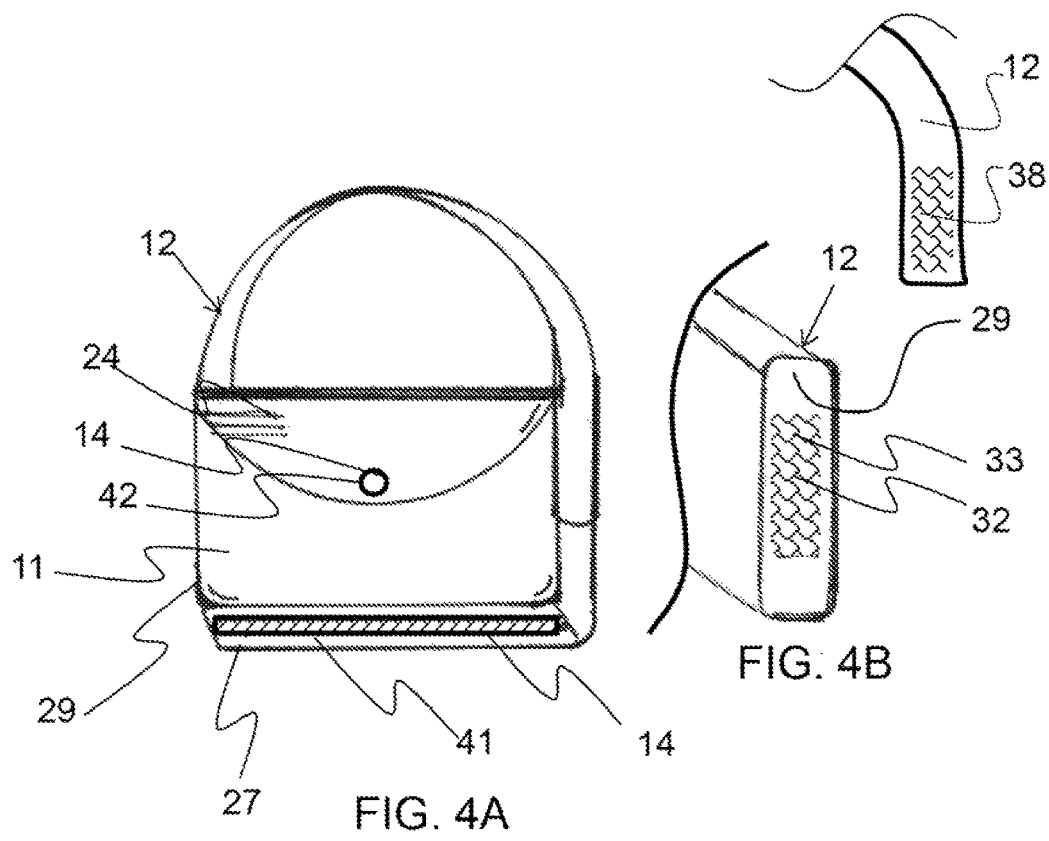
FIG. 4A
FIG. 4B

THERAPUETIC PURSE

CROSS REFERENCE TO RELATED APPLICATIONS

This application claims the benefit of U.S. provisional patent application No. 61/665,670, filed on Jun. 28, 2012, which is incorporated herein by reference in its entirety.

BACKGROUND OF THE INVENTION

Field of the Invention

The present invention relates to therapeutic purses.

Background

Breast surgery, including biopsy, mastectomy and the like require a long recovery with pain and discomfort. Many women have to return to work or other daily activities before the pain and/or swelling from the surgery has subsided. Application of heat or cold to the affected area may be recommended for quicker recovery and for pain management. However, application of a hot or cold pad in public may be embarrassing and may prevent women from performing normal activities. In addition, some women may benefit from the use of a pillow or cushion applied to the affected area.

There exists a need for a discrete way of carrying a pillow or cushion for therapy. In addition, there exists a need for a device that will allow for discrete application of hot or cold to an affected area, especially the breast region.

SUMMARY OF THE INVENTION

The invention is directed to a therapeutic purse configured with a therapeutic device, including a cushion or a thermal pouch. The therapeutic purse is an enclosure having an interior volume and at least one opening to the interior volume and a closure feature. In one embodiment, the interior volume of the purse comprises a therapeutic pocket configured for containing a therapeutic device.

The therapeutic purse described herein, comprises an attached strap. The strap may be configured with at least one end that can be detachably attached to the purse, and in one embodiment comprises a first side of a hook and loop fastener, while the purse comprises a second side of a hook and loop fastener. The strap may be configured in any suitable way to be detachably attached to the purse. For example, the strap may at least one of a first or second end that is configured with a button, snap, latch or any other suitable detachable attachment device. In a preferred embodiment, the strap is configured to be adjustable in length, thereby allowing a user to configure the purse for over the shoulder wear, or for across the chest wear. The strap may comprise a clip or any other feature that allows an end of the strap to be doubled over and retained in a generally parallel configuration with a second length of the strap, and retained in the clip. The strap may have any suitable length including, but not limited to, greater than about 0.25 m, greater than about 0.5 m, greater than about 0.75 m, greater than about 1.0 m, greater than about 1.25 m, greater than about 1.5 m, and any range between and including the lengths provided. The strap may have any suitable width including, but not limited to, greater than about 1 cm greater than about 2.5 cm, greater than about 5 cm, greater than about 7.5 cm, greater than about 10 cm, greater than about 12.5 cm, and any range between and including the widths provided.

The therapeutic purse described herein, comprises at least one therapeutic device including a cushion or a thermal pouch. A cushion may comprise any suitable type of material including, but not limited to, foam, beads, feathers, liquid, air, synthetic polymeric materials, and the like. In many cases, the cushion material may be enclosed in a cushion enclosure to form a pillow. A thermal pouch may be either a cold or a hot pouch. The pouch may be a plastic enclosure that is liquid proof, and cold or hot water may be comprised therein. Any suitable cold or hot substance may be included in the thermal pouch including, but not limited to, water, ice, oil, gel, chemicals that may be selected to chemically react in an endothermic or exothermic manner, and the like. In one embodiment, a user may activate the chemical reaction and then insert the thermal pouch into a therapeutic pocket, for example. In yet another embodiment, a separate hot or cold therapeutic device may be inserted into a therapeutic pocket. For example, a person may insert a cold pack into a therapeutic pocket.

A thermal pouch may be configured to be coupled with a conduit in the strap, thereby allowing the cold or hot substance within the thermal pouch to be transferred into the conduit. This configuration may allow for more direct application of a thermal substance to an affected area. For example, a user may insert a cold thermal pouch containing chilled water into the therapeutic purse, and connect the strap conduit to the pouch. The user may then adjust the strap to wear the purse across the chest. The chilled water would then be allowed to move into the strap conduit. The user may simply squeeze the therapeutic purse to force the chilled liquid into the strap conduit.

The strap conduit may be coupled to the strap in any suitable way, and may be enclosed within the strap, and/or may be detachably attached to the strap. The conduit may extend the length of the strap and may be configured such that both a first and second end of the conduit are coupled to the thermal pouch. In this manner, the substance within the thermal pouch may be transferred through the entire length of the strap. However, the affected area may be more localized and therefore, it may be more effective and comfortable for the user to have the conduit configured to extend only along a portion of the strap. For example a conduit having a first and second end may be configured in a loop, with both ends extending from the same end of the strap. In another configuration, the conduit is configured in a serpentine configuration to more effectively distribute the hot or cold substance over the width of the strap. In yet another embodiment, a conduit is configured in a reservoir configuration, having only one end extending from the strap and the other end closed, thereby creating a reservoir for the hot or cold substance.

A conduit may be made of any suitable material including, but not limited to, plastic, metal, combinations thereof and the like. The conduit may comprise material and be configured in a way to effectively transfer heat or cold to the user. A conduit may have any suitable geometry such as round, flat, oval and the like. In addition, a conduit may change geometry, including wall thickness, and material types over the length of the conduit, to more effectively deliver the hot or cold substance without excessive heat loss. For example, when a conduit is configured to extend the length of the strap a first length of the conduit may be configured with a first wall thickness and a first thermal set of properties, and a second length of the conduit may be configured with a second wall thickness and a second thermal set of properties. The second length of conduit may have a thickness that is substantially greater than the first wall thickness, thereby reducing thermal transfer in the second length. In addition, any type or combination of materials may be used over any portion of the strap. For example, portions of the strap that are not configured to contact a therapeutic site may comprise thermal insulating materials to reduce transfer of the heat or insulate cooling medium contained there. Portions of the strap that are configured to contact a therapeutic site, such as laying over the chest region, may be comprise thermal conducting materials to better transfer the heat or cold to the wearer. Furthermore, a plurality of conduits may be used, or a single conduit may branch into two or more conduits.

A therapeutic purse may further comprise a pump device, whereby the pump is configured to pump fluid from said thermal pouch through or into a conduit. A pump device may be configured for insertion into the interior volume of the therapeutic purse, or into a therapeutic pocket. A pump may be coupled to a thermal pouch, to a conduit, or between a thermal pouch and conduit. Any suitable type of pump device may be used including, but not limited to, a diagram pump, peristaltic pump, positive displacement pump, and the like. A pump device may be powered by a battery, and should be configured to be small enough and lightweight enough to be inserted into the therapeutic purse as described herein.

The therapeutic purse and strap as described herein, may be configured in any suitable way to couple the conduit to a thermal pouch. For example, a therapeutic purse may comprise an opening in at least one end of the purse whereby a conduit may be passed therethrough. In one embodiment, one end of a therapeutic purse comprises a conduit opening and the other end of the purse comprises a detachable attachment feature for attaching and/or adjusting the length of the strap. A conduit opening may be configured in a side, the top or bottom of the therapeutic purse.

A therapeutic purse comprises an enclosure having an interior volume and at least one interior opening to the interior volume and a closure feature. An interior opening may be configured in any suitable location, such as along the top or bottom of the purse. In one embodiment, the opening is along the bottom of the purse and comprises a hook and loop closure feature. A hard closure feature, such as a zipper, configured along the top of the therapeutic purse may be uncomfortable to the user, especially if the top of the purse touches an therapeutic site, or affected area.

The summary of the invention is provided as a general introduction to some of the embodiments of the invention, and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
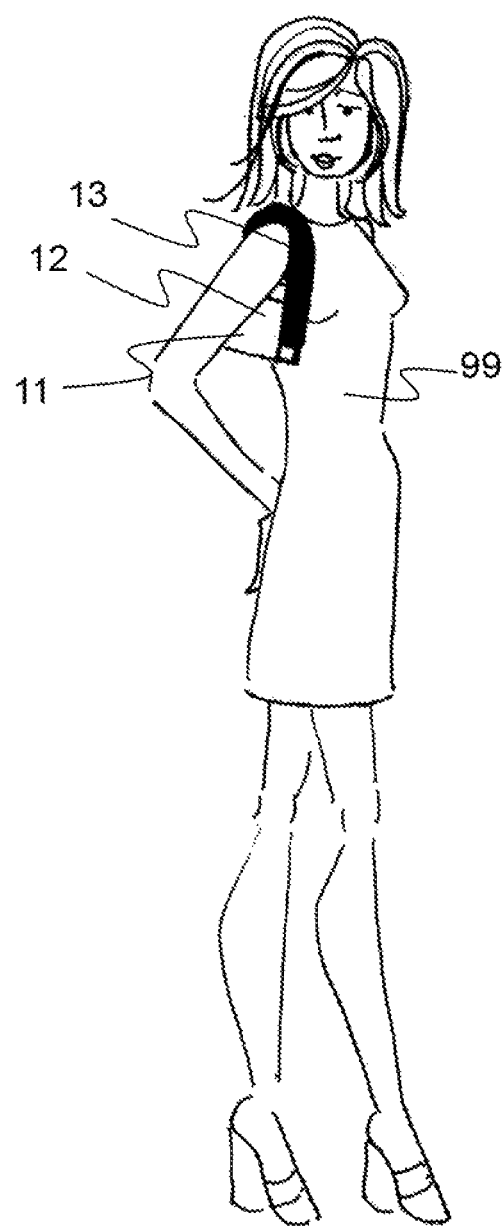

FIG. 1 shows a perspective view of a user having a therapeutic purse in an over the shoulder configuration.

Figure 2:
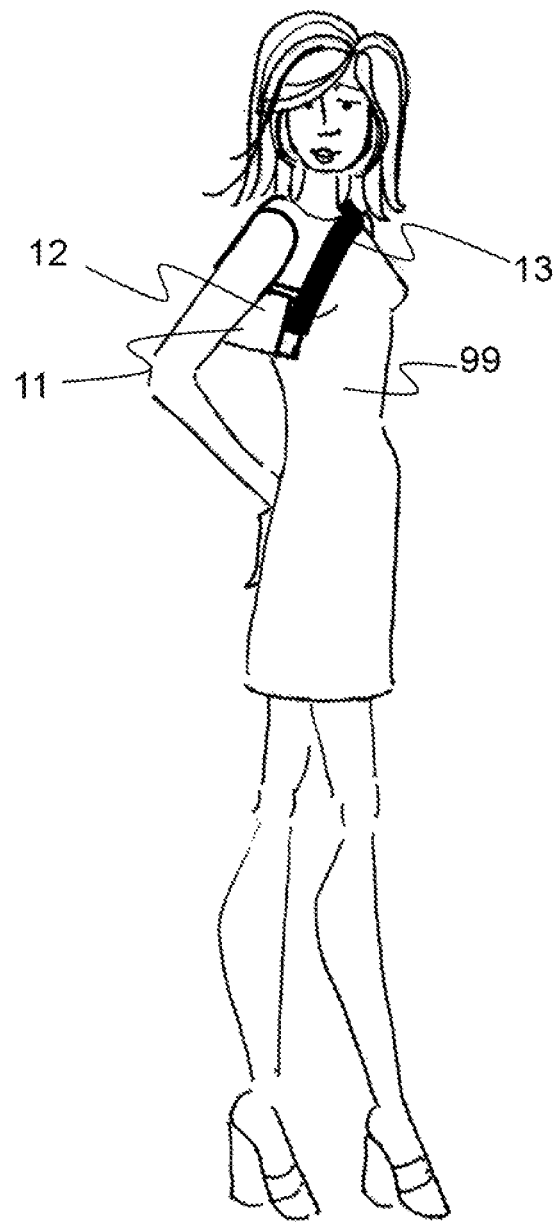

FIG. 2 shows a perspective view of a user having a therapeutic purse in an across the chest configuration.

FIG. 3 shows a perspective view of an exemplary therapeutic purse having an interior opening configured along the top of the purse.

FIG. 4A shows a perspective view of an exemplary therapeutic purse having an interior opening configured along the bottom of the purse.

FIG. 4B shows a perspective view of an end of the exemplary therapeutic purse shown in FIG. 4A having a hook and loop fastener.

Figure 5:
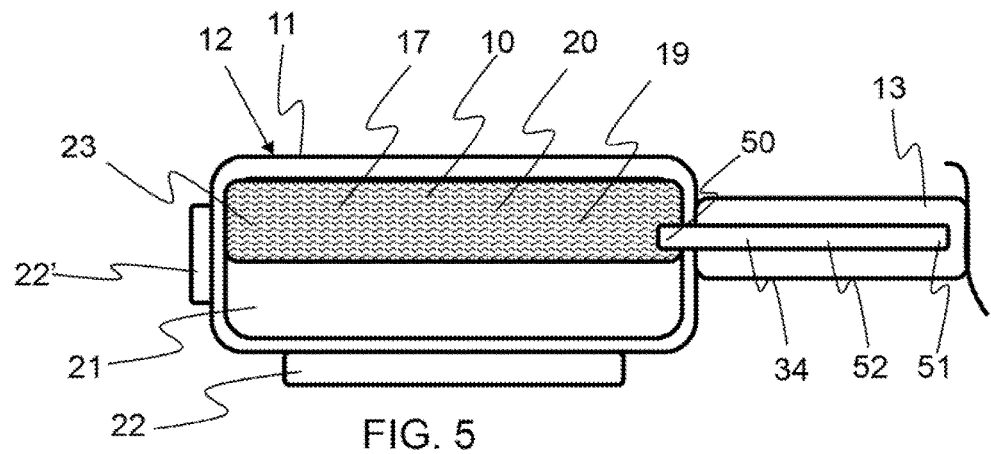

FIG. 5 shows a top down view of an exemplary therapeutic purse having a cold pouch in a therapeutic pocket, and a conduit coupled thereto.

Figure 6:
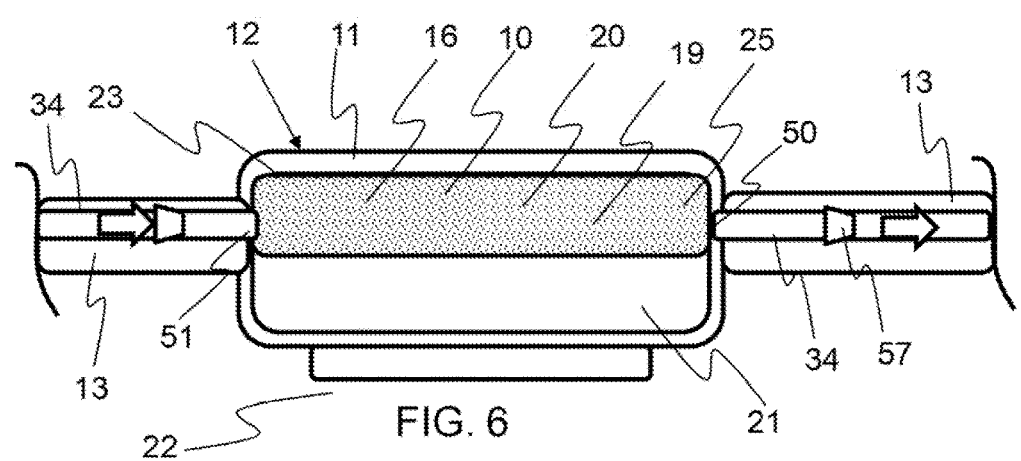

FIG. 6 shows a bottom up view of an exemplary therapeutic purse having a hot pouch in a therapeutic pocket, and a conduit coupled thereto.

Figure 7:
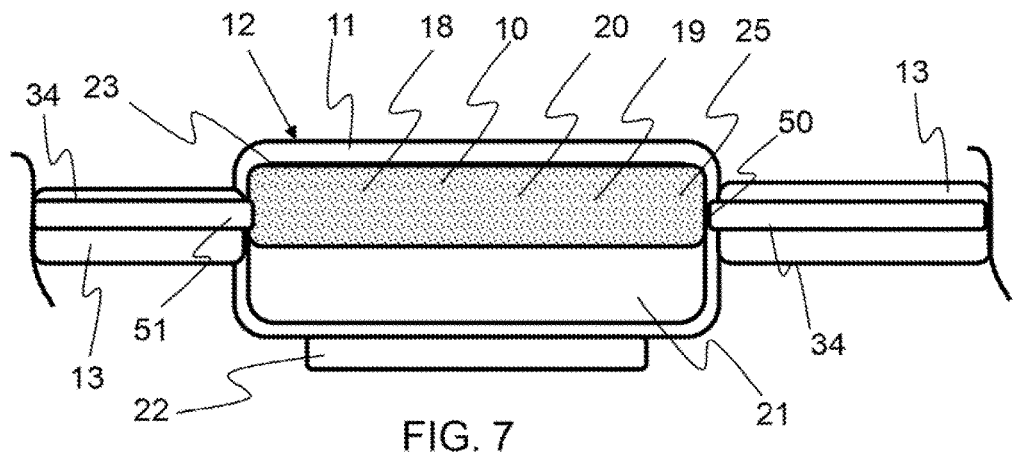

FIG. 7 shows a bottom up view of an exemplary therapeutic purse having a cushion in a therapeutic pocket.

Figure 8:
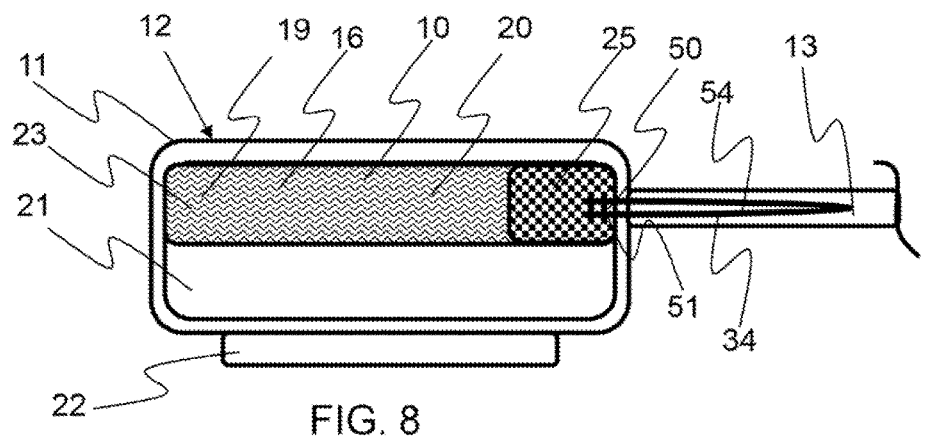

FIG. 8 shows a top down view of an exemplary therapeutic purse having a hot pouch and a pump device in a therapeutic pocket, and a conduit coupled thereto.

Figure 9A:
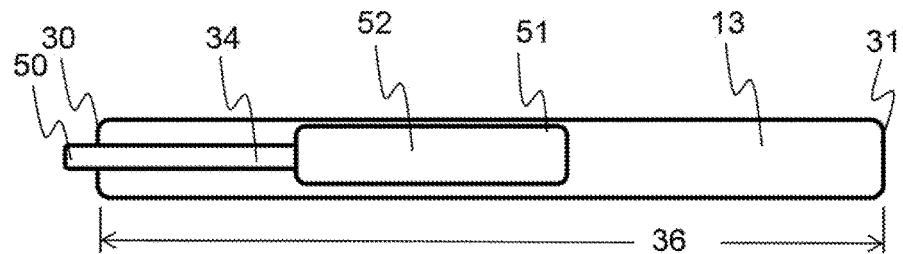

FIG. 9A shows a top down view of a strap and reservoir type conduit.

Figure 9B:
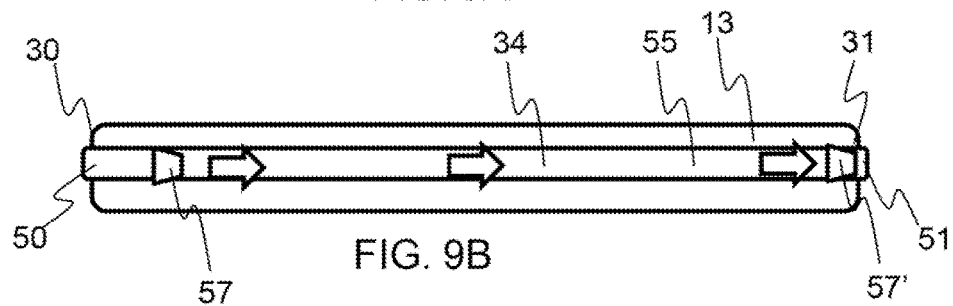

FIG. 9B shows a top down view of a strap and a conduit extending the length of the strap.

Figure 9C:
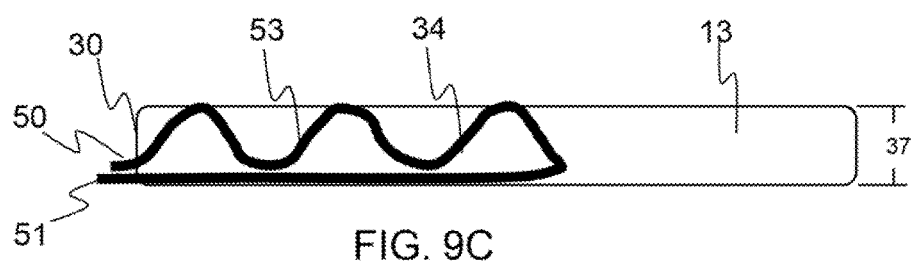

FIG. 9C shows a top down view of a strap and serpentine type conduit.

Figure 10A:
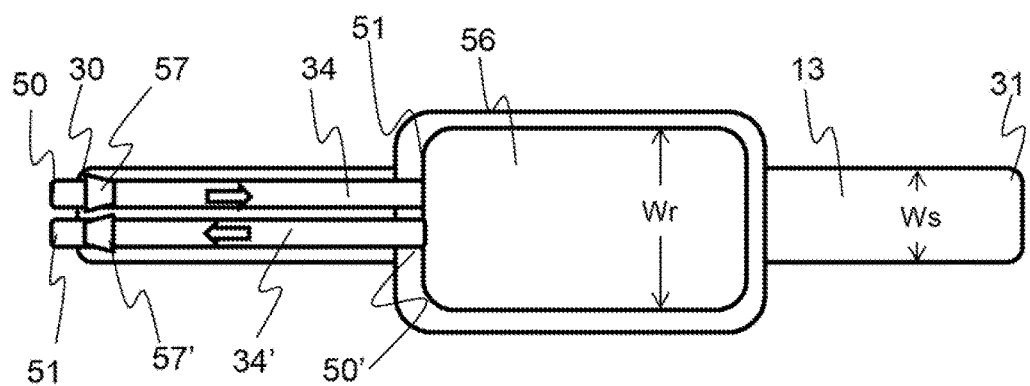
Figure 10B:
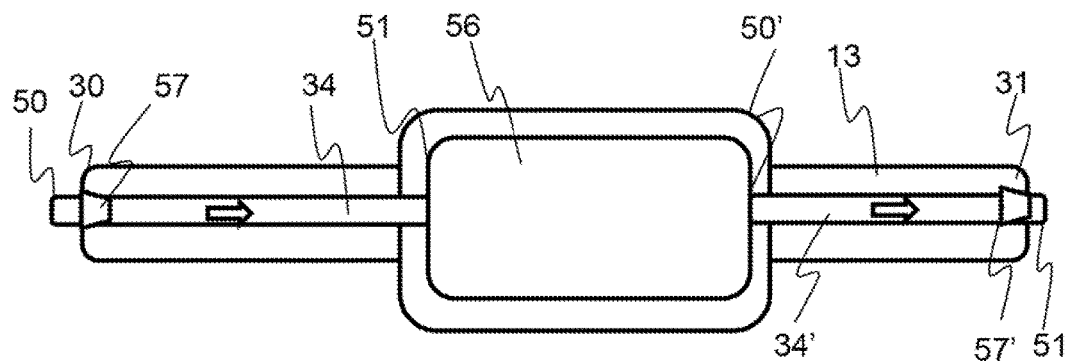

FIGS. 10A and 10B show a top down view of a strap having an open reservoir configured along the length of the strap.

Figure 11:
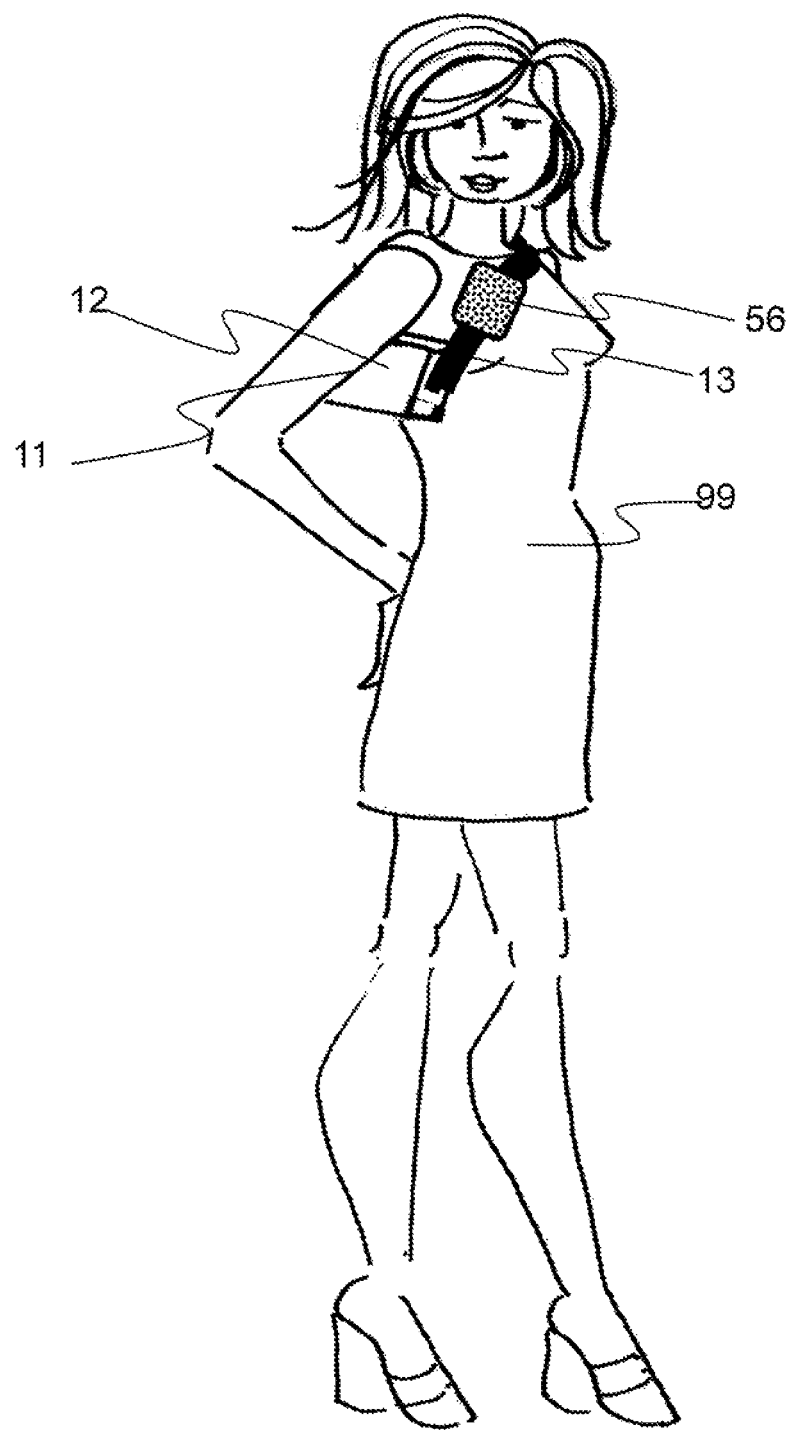

FIG. 11 shows a perspective view of a user having a therapeutic purse in an across the chest configuration with an open reservoir configured over her chest area.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for the purpose of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications and improvements are within the scope of the present invention.

As shown if FIG. 1, a user 99 is wearing a therapeutic purse 12 in an over-the-shoulder configuration. The strap 13 is attached to the purse enclosure 11. As shown in FIG. 2, a user 99 is wearing a therapeutic purse 12 in an across the chest configuration. The strap 13 is attached to the purse enclosure 11 and extends across the user's chest.

As shown in FIG. 3, a therapeutic purse 12 comprises an enclosure 11 and a strap 13. In this exemplary embodiment, a zipper type 40 closure feature 14 is configured along the top 26 of the purse. In addition, an exterior pocket 22 is configured on one side 28 of the therapeutic purse, and has a flap as a pocket closure 24. A flap may be configured to extend from one side of the purse to the other side of the purse, thereby extending over the top and/or bottom of the purse. The strap 13 is attached at either end 29 of the therapeutic purse. A snap type attachment device 32 is shown attaching the strap 13 to the enclosure 11.

As shown in FIG. 4A, the therapeutic purse comprises a hook and loop type 41 closure feature 14 along the bottom 27 of the purse. In addition, the exterior pocket 22 is configured on one side 28 of the therapeutic purse, and has a flap as a pocket closure 24 with a snap type closure feature 14.

As shown in FIG. 4B, an end 29 of a therapeutic purse 12 is configured with a first side 33 of a hook and loop type attachment device 41. A strap 13 having the second side 38 of the hook and loop attachment device 41 may be detachably attached to the therapeutic purse 12. Any suitable type of attachment device 32 may be used including a button, snaps and the like.

As shown in FIG. 5, an exemplary therapeutic purse 12 comprises an enclosure 11, having an interior volume 20. The interior volume 20 of the therapeutic purse 12, comprises a cold pouch 17 type thermal pouch 10 coupled to a conduit 34 that is attached to a strap 13. The first end of the conduit 51 is coupled to the thermal pouch, whereby fluid from the thermal pouch can flow into the conduit 34. The conduit in this configuration is closed reservoir type 52, having a closed conduit second end 51 that is located along the length of the strap 13. Also shown in FIG. 5, is an interior pocket 21 and an exterior pocket 22. A second exterior pocket 22' is configured on one end of the enclosure 11. Any number and configuration of interior and exterior pockets may be configured in the therapeutic purse, as described herein.

As shown in FIG. 6, an exemplary therapeutic purse 12 comprises an enclosure 11, having an interior volume 20 comprising a hot pouch 16 type thermal pouch 10 coupled to a conduit 34, that is attached to a strap 13. The conduit in this configuration extends along the length of the strap 13, and both the first 50 and second 51 conduit end are coupled to the hot pouch 16. The first end 50 of the conduit 34 is coupled on one side of the thermal pouch and the second end 51 is couple to the opposing end of the thermal pouch. The conduit 34 extends along substantially the entire length of the strap. A valve 57, in this configuration, is coupled to the conduit to allow for flow of the hot pouch substance in only one direction, as indicated by the arrows. In this configuration, a person may simply squeeze the thermal pouch to force the pouch substance through the conduit.

As shown in FIG. 7, an exemplary therapeutic purse 12 comprises an enclosure 11 having an interior volume 20 comprising a cushion 18 type therapeutic device 19. A cushion type therapeutic device may be free standing material, such as a foam, or may be enclosed to form a pillow. A cushion may substantially fill the interior volume 20 of the enclosure 11, or may fill a portion, as shown in FIG. 7.

As shown in FIG. 8, an exemplary therapeutic purse 12 comprises an enclosure 11 having an interior volume 20 comprising a hot pouch 16 type thermal pouch 10, and a pump device 25. The pump device is configured between the conduit 13 and the thermal pouch 10. The conduit in this exemplary embodiment, is in a loop type 54 configuration, having both the first 50 and second conduit ends 51 at the same end of the strap 13.

As shown in FIG. 9A, a first conduit end 50, of a conduit 34 extends from a first end 30 of a strap 13. The conduit is a closed reservoir type 52 conduit, having a second end 51 that is closed. The strap length 36 is shown in FIG. 9A. The conduit 34 extends only a portion of the length of the strap 13.

As shown in FIG. 9B, a flow through type 55 conduit 34 extends the length of the strap and has a first end 50 extending from the first end 30 of the strap and a second end 51 extending from the second end 31 of the strap. A valve 57 is shown allowing for flow in into the conduit 34. A second valve 57' is shown allowing for flow out of the conduit 34. These valves may be one way flow valves, whereby squeezing the enclosure of the therapeutic purse creates a flow into and out of a conduit configured in a strap 13. Again, the conduit may extend from one end of the first end 30 of the strap to the second end 31 of the strap. In another embodiment, the conduit extends into and out of the same end of the strap. In still another embodiment, a first conduit extends to a As shown in FIG. 9C, a serpentine type 53 conduit 34 is configured on a strap 13. A serpentine type conduit may be used to more effectively distribute the thermal substance over the strap width 37. A serpentine type 53 conduit 34 may extend the length of the strap or may loop back as shown in FIG. 9C.

As shown in FIG. 10A, an open reservoir 56 is configured along a strap 13. The open reservoir and strap in the location of the open reservoir are wider, having a reservoir width Wr, that is greater than the width of the remainder of the strap Ws. A first conduit 34 is configured to provide fluid flow to the open reservoir 56 and comprises a valve 57 that allows liquid flow from the thermal pouch (not show), to the open reservoir. A second conduit 34' is configured to return fluid from the open reservoir 56 to the thermal pouch and may comprise a one-way valve 57' as shown in FIG. 10A. The valves may be configured at the end of the conduits, or along the length of the conduit. The first and second conduits are configured on the same side of the strap in FIG. 10A. The open reservoir may have any suitable configuration and may be located in any suitable location along the length of the strap. In a preferred embodiment, the strap has an adjustable length, whereby a user can position a reservoir in a location that places the reservoir over an area of the body that requires therapy, as shown in FIG. 11. In FIG. 11, the user 99, has positioned the open reservoir 56 over a portion of the body needing therapy. A cold or hot fluid may be pumped into the open reservoir by simply squeezing the enclosure portion of the purse, for example. A user may also be able to empty the open reservoir by squeezing the open reservoir.

As shown in FIG. 10B, a first conduit, for fluid delivery, extends along one side of the strap from the thermal pouch (not shown) to the open reservoir and a second conduit 34', for fluid return to the thermal pouch, on the other side of the strap. It is to be understood that any suitable configuration and combination of conduits and reservoirs may be used in therapeutic device of the present invention. For example, a serpentine type conduit may extend from the therapeutic device, such as a hot fluid reservoir or heat pouch, to an open reservoir.

Any suitable combination of conduit configurations and types may be used. A conduit may change type along the length of the strap, and may also change shape, wall thickness and/or material type along the length of the conduit. A conduit may extend out from the strap in any suitable location and couple with the thermal pouch. A conduit may be configured with a pouch that extends along at least a portion of the length of the strap and may comprise a closable slit in said pouch for extending the conduit out from the pouch. For example, a pouch may extend along the length of a strap and at the ends of the strap, a slit having a hook and loop fastening feature may allow the conduit to be extended out from the strap. The slit may extend any suitable length along the length of the strap. A conduit may be configured to be detachably attached or coupled with a thermal pouch. Any suitable detachable feature may be used, such as those used, on hydration bladders which have a quick disconnecting feature.

As used herein, the term coupled means that one item is attached to or configured on another item, article or feature. For example, a conduit may be coupled to a pump through a hose barb, or quick-connect fitting.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A therapeutic purse comprising:
   a. an enclosure comprising;
      i. an interior volume; and
      ii. a closure feature;
      iii. a top;
      iv. a bottom;
   b. a therapeutic device comprising a thermal pouch;
   c. a strap having a length,
   d. a conduit coupled to the strap;
   wherein the strap is attached to said therapeutic purse; and
   wherein the thermal pouch is coupled to at least one end of said conduit;
   whereby a liquid within said thermal pouch can be transferred from said thermal pouch into said conduit; and
   wherein the closure feature is configured on said bottom.

2. The therapeutic purse of claim 1, wherein the strap comprises a first and second end and wherein at least one end of the strap is configured to be detachably attached to said enclosure.

3. The therapeutic purse of claim 2, wherein the strap comprises a first side of a hook and loop fastener and the enclosure comprises a second side of a hook and loop fastener, thereby providing for detachably attaching the strap to said enclosure.

4. The therapeutic purse of claim 1, wherein the thermal pouch is a hot pouch.

5. The therapeutic purse of claim 1, wherein the thermal pouch is a cold pouch.

6. The therapeutic purse of claim 1, further comprising a valve coupled to the conduit.

7. The therapeutic purse of claim 1, wherein the conduit is configured within the strap.

8. The therapeutic purse of claim 1, wherein the conduit has a first end and a second end, wherein the conduit extends along the length of the strap from said first end that is coupled with the thermal pouch to said second end that is coupled with said thermal pouch.

9. The therapeutic purse of claim 1, wherein the conduit is configured in a loop configuration, having a first conduit end and a second conduit end extending from the same end of said strap and coupled with the thermal pouch.

10. The therapeutic purse of claim 1, wherein the conduit is configured in a serpentine configuration along at least a portion of the length of the strap.

11. The therapeutic purse of claim 1, wherein the conduit is configured in a reservoir configuration, a first end coupled with the thermal pouch and a second end terminating along the length of the strap.

12. The therapeutic purse of claim 1, wherein the conduit has an enlarged area between a first end and a second end to form a reservoir along the length of the strap.

13. The therapeutic purse of claim 1, comprising an open reservoir configured along the length of the strap, wherein a first conduit extends from the thermal pouch to said open reservoir for transferring a fluid from said thermal pouch to said open reservoir, and a second conduit extends from said open reservoir back to said thermal pouch for returning fluid from said open reservoir to said thermal pouch.

14. The therapeutic purse of claim 1, further comprising a pump device, whereby the pump is configured to pump fluid from said thermal pouch through said conduit.

15. The therapeutic purse of claim 1, wherein the interior volume comprises a therapeutic pocket, configured for containing the therapeutic device.

16. The therapeutic purse of claim 15, wherein the therapeutic pocket is liquid-proof.

17. The therapeutic purse of claim 1, further comprising a pump device configured to pump said liquid from the thermal pouch into the conduit.

* * * * *